United States Patent

Uchida et al.

Patent Number: 5,494,804
Date of Patent: Feb. 27, 1996

[54] DIFFERENTIAL DETERMINATION PROCESS OF α-AMYLASE ISOENZYME ACTIVITIES

[75] Inventors: Riichiro Uchida; Shoichi Tokutake; Nobuyuki Yamaji, all of Noda; Yoshinori Motoyama; Kenji Hosoi, both of Tokyo, all of Japan

[73] Assignees: Kikkoman Corporation, Noda; Daiichi Pure Chemicals Co., Ltd., Tokyo, both of Japan

[21] Appl. No.: 305,917

[22] Filed: Sep. 16, 1994

[30] Foreign Application Priority Data

Oct. 20, 1993 [JP] Japan .................. 5-262727
May 11, 1994 [JP] Japan .................. 6-097214

[51] Int. Cl.⁶ .................. C12Q 1/34; C12Q 1/00; C12Q 1/40; C07G 3/00
[52] U.S. Cl. .................. 435/18; 435/4; 435/22; 435/14; 536/4.1; 536/18.5; 536/1.11
[58] Field of Search .................. 435/18, 22, 4, 435/14; 536/4.1, 17.1, 18.5, 1.11

[56] References Cited

U.S. PATENT DOCUMENTS

| | | | |
|---|---|---|---|
| 4,000,042 | 12/1976 | Adams | 435/22 |
| 4,945,043 | 7/1990 | Gerber | 435/22 |
| 5,264,345 | 11/1993 | Schmidt et al. | 435/4 |
| 5,302,514 | 4/1994 | Takutake et al. | 435/22 |
| 5,314,803 | 5/1994 | Wilk et al. | 435/4 |
| 5,350,678 | 9/1994 | Ikenaka et al. | 435/22 |
| 5,378,831 | 1/1995 | Usui et al. | 536/4.1 |

FOREIGN PATENT DOCUMENTS

| | | |
|---|---|---|
| 386701 | 4/1991 | Japan . |
| 390095 | 4/1991 | Japan . |
| 4229196 | 8/1992 | Japan . |
| 2257139 | 6/1993 | United Kingdom . |

OTHER PUBLICATIONS

J. Biochem. 84, 835–841 (1978).
Carbohydrate Research, 51, 73–84 (1976).

*Primary Examiner*—Michael G. Wityshyn
*Assistant Examiner*—Louise N. Leary
*Attorney, Agent, or Firm*—Birch, Stewart, Kolasch & Birch

[57] ABSTRACT

A process for differentially determining α-amylase isoenzyme activities by the inhibitor method, in which $6^3$-deoxymaltotriose (DOG3) represented by the formula

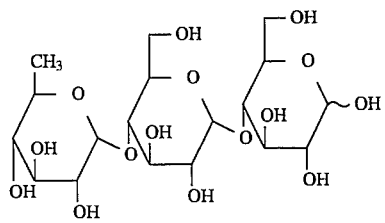

is used as an inhibitor.

8 Claims, 4 Drawing Sheets

DIFFERENTIAL DETERMINATION PROCESS OF α-AMYLASE ISOENZYME ACTIVITIES

FIELD OF THE INVENTION

The present invention relates to a novel differential determination process of α-amylase isoenzyme activities, more particularly to a process for differentially determining α-amylase isoenzyme activities in a sample in an easy operation with precision by the inhibitor method using a novel inhibitor.

DESCRIPTION OF THE PRIOR ART

It is known that a human α-amylase generally includes the two isoenzymes, the one of which is derived from pancreas (referred to hereinafter as P-type α-amylase), the other derived from salivary gland (referred to hereinafter as S-type α-amylase).

Early stage of acute pancreatitis or severity of chronic pancreatitis are suspected at a high level of total α-amylase activity in serum, which is mainly caused by the increase of P-type α-amylase activity. However, intensive increase of total α-amylase activity is observed also in the diseases of salivary gland or parotid gland, in post-surgical operation as well as in some hepatic diseases due to mainly the increase of S-type α-amylase activity, which may often lead to a wrong diagnosis. Thus, a simple and precise method for differentially determining these isoenzymes has sincerely been requested in these years.

There have hitherto been known as the differential determination method of human α-amylase isoenzyme activities, for example (1) electrophoresis, (2) gel filtration, (3) enzyme immunoassay (EIA), or (4) inhibitor method using an inhibitor such as wheat-germ inhibitor.

Among these methods, the methods (1)–(3) have a defect in that measurement operation is complicated and requires a long period of times.

On the other hand, the inhibitor method (4) using a wheat-germ inhibitor as an inhibitor is to determine the activities of P-type and S-type α-amylases, by employing the fact that said wheat-germ inhibitor inhibits the S-type α-amylases more strongly than the P-type α-amylases, in other words, these inhibition have different inhibiting constants against these amylases. This method, which is relatively simple for handling, has been increasingly used in these years.

However, the wheat-germ inhibitor is an protein and thus poor in stability. Accordingly, it is difficult to store for a long period a kit of reagents for measuring the activity of α-amylase isoenzymes. Moreover, the wheat-germ inhibitor has also a defect that the inhibiting constant of the wheat-germ inhibitor must be measured for each kit, since the wheat-germ inhibitors to α-amylase isoenzymes have different inhibiting constants depending on their purification degrees.

SUMMARY OF THE INVENTION

The present invention has been done for the purpose of overcoming the defects in the conventional inhibitor method and providing a method for measuring the α-amylase isoenzyme activities efficiently, in a simple operation and at a high precision.

The present inventors have carried out a variety of researches for the purpose of accomplishing the aforementioned object. As a result, they have found that there is very large difference between inhibiting constants of $6^3$-deoxymaltotriose to P-type and S-type α-amylases and that the differential determination of α-amylase isoenzymes by the inhibitor method may be successfully accomplished by using the aforementioned material as an inhibitor. They have thus accomplished the present invention on the basis of these findings.

That is to say, the present invention is to provide a differential quantitative determination process of α-amylase isoenzyme activities with use of a measured value of an α-amylase activity obtained by reacting a substrate for measuring the α-amylase activity with a sample and a measured value of an α-amylase activity obtained by reacting the same substrate and sample as above in the presence of an inhibitor which has different inhibiting constants against two kind of α-amylase isoenzymes, the so-called, which comprises using inhibitor method, $6^3$-deoxymaltotriose [O-6-deoxy-α-D-glucopyranosyl-(1→4)-O-α-D-glucopyranosyl-(1→4)-D-glucose] represented by the formula as an inhibitor.

The present invention is now explained in detail below.

First, the substrate for measuring α-amylase activities used in the present invention may be any substrates which may measure α-amylase activities, and includes for example, a maltooligosaccharide derivative represented by the general formula wherein R represents a hydrogen atom, an aromatic chromogenic group or a saccharide group except glucose, $R^1$ and $R^2$, which may be the same or different, represent a halogen atom, hydroxyl, azido, acyloxy, alkyloxy, aryloxy, alkylsulfonyl, arylsulfonyl, alkylmercapto, arylmercapto, N-alkylcarbamoyloxy, N-arylcarbamoyloxy, alkyloxymethoxy or aryloxymethoxy group, or $R^1$ and $R^2$ may form together a substituted or unsubstituted methylenedioxy group, and n denotes an integer of 1–6.

Among these materials, the one having a ratio of reaction rates of P-type and S-type α-amylases to the substrate being at least 0.6, especially about 1 is advantageous in simplicity, easiness and exactness.

Also, $6^3$-deoxymaltotriose represented by the formula (I) which is used as an inhibitor is not substantially hydrolyzed by α-amylase or even by a coupled enzyme which may exist on measuring the α-amylase activities, if necessary, and specifically inhibits particularly the P-type α-amylase. Thus, the difference of the inhibiting constants of the P-type and S-type α-amylases is very large. Furthermore, this material which is different from the other proteins such as wheat-germ inhibitor is highly stable, so that it can be stored for a long period and used effectively when it is incorporated as a reagent kit for measuring α-amylase isoenzyme activities.

Next, the process for differentially determining α-amylase isoenzyme activities in a sample is explained specifically.

Reaction rate constants ($k_p$, $k_s$) to a substrate for measuring α-amylase activities used are first obtained with P-type and S-type α-amylases preparations having a known activity, respectively, by the ordinary manner (see Examples below).

Also, $6^3$-deoxymaltotriose used as an inhibitor is added in various concentrations to the same substrate for measuring α-amylase activities as the one used above to determine the concentration of $6^3$-deoxymaltotriose at which the difference of the inhibiting constants to the above-described P-type and S-type α-amylase preparations maximizes, and the inhibition constants (a, b) to P-type and S-type α-amylases at this concentration are found by the ordinary method (see Examples below).

Next, the aforementioned substrate for measuring α-amylase activities is added to a sample of which α-amylase activities are measured. Reaction of the mixture is carried out in the presence or absence of a coupled enzyme by the ordinary manner and the variable absorbances (T) are measured.

Variable absorbance (W) is next measured in the same manner as mentioned above except that $6^3$-deoxymaltotriose in the concentration determined above is added.

In this connection, the following relationship exists between the P-type α-amylase activity (P) and the S-type α-amylase activity (S):

$$k_p P + K_s S = T \qquad (1)$$

$$(1-a) k_p P + (1-b) k_s S = W \qquad (2)$$

The following equations are obtained from these relationships:

$$P = [(1-b) T - W]/[k_p (a-b)] \qquad (3)$$

$$S = (T - k_p P)/k_s \qquad (4)$$

That is to say, if $k_p$, $k_s$, a and b are preliminarily measured, the differential determination of the two isoenzyme activities in a sample can be easily carried out by using a substrate for measuring α-amylase activities and the same substrate and $6^3$-deoxymaltotriose, and by substituting the variable absorbance (T, W) measured in the enzyme reaction with a sample for T and W in the formulae (3) and (4).

The $6^3$-deoxymaltotriose represented by the formula (I) which is used in the process of the present invention may be either the α-anomer or the β-anomer.

Also, the maltooligosaccharide derivative represented by the formula (II) which is used as the substrate for measuring the α-amylase activities may be either the α-anomer or the β-anomer. Moreover, as the moiety of maltooligosaccharide, all of those including, for example, from maltotriose to maltooctaose may be used, particularly maltopentaose, maltohexaose and maltoheptaose are preferred.

The group R in the general formula (II) represents a hydrogen atom, an aromatic chromogenic group or a moiety of a monosaccharide except glucose, particularly the aromatic chromogenic group is preferred.

As the aromatic chromogenic group, there may be used any spectroscopically detectable ones including, for example, the followings:

wherein $R^3$–$R^7$, which may be the same or different, represent a hydrogen atom, a halogen atom, nitro, alkyl, aryl, allyl, amino, sulfonic acid or carboxyl group, or $R^3$ and $R^4$ or $R^4$ and $R^5$ may be bonded together to form a fused aromatic ring, wherein $R^8$ represents a hydrogen atom or an alkyl group, wherein $R^9$ represents a hydrogen atom or an alkyl group, and wherein $R^{10}$–$R^{17}$, which may be the same or different, represent a hydrogen atom, a halogen atom, nitro, alkyl, aryl, allyl, amino, sulfonic acid or a carboxyl group, or $R^{10}$ and $R^{11}$ or $R^{12}$ and $R^{13}$ may be bonded together to form a fused aromatic ring, or $R^{11}$ and $R^{12}$ and/or $R^{15}$ and $R^{16}$ may represent a common oxygen atom to form a fused ether ring, and Z represents a nitrogen atom or a group N→O.

Furthermore, the monosaccharide except glucose may be a monosaccharide in a wide sense or a derivative thereof and includes, for example, fructose, inositol, glucitol, sorbitol and glucose-6-phosphate.

Typical examples of the compound represented by the general formula (II) include maltopentaose, maltoheptaose, 2-chloro-4-nitrophenyl β-D-maltopentaoside, 2-chloro-4-nitrophenyl $4^5,6^5$-di-O-(N-ethyl)carbamoyl-β-D-maltopentaoside, 2-chloro-4-nitrophenyl $4^5,6^5$-di-O-methoxymethyl-β-D-maltopentaoside, 2-chloro-4-nitrophenyl $6^5$-azido-$6^5$-deoxy-β-D-maltopentaoside, 2-chloro-4-nitrophenyl $6^7$-chloro-$6^7$-deoxy-β-D-maltoheptaoside, 2-chloro-4-nitrophenyl α-D-maltotrioside, 4-nitrophenyl $6^5$-O-benzyl-α-D-maltopentaoside, 2-chloro-4-nitrophenyl $4^5,6^5$-O-benzylidene-β-D-maltopentaoside, phenolindo-3'-chlorophenyl $6^5$-O-toluenesulfonyl-β-D-maltopentaoside, $6^5$-chloro-$6^5$-deoxy-D-maltopentaose, 1-($4^6$-O,$6^6$-O-dimethanesulfonyl-α-maltohexaosyl)-α-D-glucitol and the like.

In this context, the symbols $6^5$, $6^7$, $6^m$ and $4^m$ herein mean that the 6- or 4-hydroxyl groups at 5th, 7th or mth from the reducing terminal in a glucose unit constituting a maltooligosaccharide derivative is substituted.

In addition, 6³-deoxymaltotriose of the formula (I) is a known material (see carbohydrate Res., 51, 73–84 (1976)), which may be prepared by any methods. For instance, the aimed 6³-deoxymaltotriose can be prepared by monotosylating β-cyclodextrin by the method described in Carbohydr. Res., 238, 193–213 (1993), reacting the tosyl derivative with sodium borohydrate to form mono-6-deoxy-β-cyclodextrin, which was reacted with an exo-type saccharification enzyme such as glucoamylase or α-glucosidase during or after the reaction with cyclodextrinase (see Japanese Patent Kokai No. 3-15384), α-amylase derived from genus Aspergillus and the like and further treating the product with an ordinary purification method. Moreover, said 6³-deoxymaltotriose may be produced by the combination of various synthesis methods (see J. Biochem., 84, 835–842 (1978)).

Furthermore, as the maltooligosaccharide derivative represented by the general formula (II), a commercially available product may be used as it is, directly or a product obtained by an appropriate combination of general preparation processes [see, for example, Japanese Patent Kokai Nos, 5-1091, 6-56869, 60-78994 and 4-346994, and Carbohydrate Research, 238,109–133 (1993)].

In the process of the present invention, α-amylase activities are measured with the maltooligosaccharide derivative represented by the general formula (II) as the substrate for measuring α-amylase activity in the presence or absence of 6³-deoxymaltotriose represented by the formula (I) as an α-amylase inhibitor for quantitatively determining the α-amylase isoenzyme activities. In this case, the α-amylase and the substrate are generally reacted in the presence of a coupled enzyme. The relationship between the substrate and the coupled enzyme is not specifically limited and may be as usual. For some substrates, coupled enzymes are not required as specified below.

For instance, there can be mentioned for the combination of the maltooligosaccharide derivative represented by the general formula (II) as the substrate and the coupled enzyme as follows:

(1) when n denotes 1 and OR represents an α-anomer, no coupled enzyme is required;

(2) in the compound wherein n denotes 2 or more and R represents a hydrogen atom (α-anomer and/or β-anomer), α-glucosidase and/or glucoamylase are employed;

(3) in the compound wherein R represents an aromatic chromogenic group or a moiety of a monosaccharide except glucose,   (i) in the case of an α-anomer alone, α-glucosidase and/or glucoamylase are employed; and   (ii) in the case of a β-anomer alone or a mixture of an α-anomer and a β-anomer, β-glucosidase is also employed in addition to α-glucosidase and/or glucoamylase.

In this connection, when the maltooligosaccharide derivative represented by the general formula (II) wherein the non-reducing terminal is a compound having hydroxyl groups for $R^1$ and $R^2$ is employed as a substrate, glucoamylase as the coupled enzyme is not employed as usual.

α-glucosidase used herein may be either of the ones derived from animals, plants or microorganisms, and the one derived from yeast is preferably used. Also, glucoamylase may be derived from any sources, and, for example, the one derived from Rhizopus sp. is preferred. Furthermore, β-glucosidase derived from any sources may be also used, and, for example, the one obtained from almond seed is employed.

Next, as systems advantageous for the quantitative determination of α-amylase isoenzyme activities, there are mentioned systems comprising the maltooligosaccharide derivative represented by the general formula (II) as the substrate in an amount of 0.1–10 mM, a buffer in an amount of 2–300 mM, and if a coupled enzyme is required, α-glucosidase and/or glucoamylase in an amount of 5–1,000 units/ml, respectively, and β-glucosidase in an amount of 0.5–30 units/ml and having pH 4–10 in consideration of the combination of said substrate and the coupled enzyme.

Also, for the concentration of the 6³-deoxymaltotriose represented by the formula (I) and incorporated as an inhibitor in the system for measuring the α-amylase activities, a concentration in which the difference between the inhibiting constants to the P-type α-amylase and the S-type α-amylase maximizes is employed, and it is generally in the concentration of 0.01–10 mM, preferably 0.05–5 mM.

As the buffer used, there are mentioned, for example, a phosphate, an acetate, a carbonate, the Good's buffer, a borate, a citrate or a dimethylglutarate.

A large variety of conventional additives may be added in addition to the aforementioned components to such systems, if necessary, in the range that will not impair the object of the present invention. For instance, there may be added glycerol, bovine serum albumin, α- or β-cyclodextrins, or Triton X-100 as a dissolution assisting agent and a stabilizing agent, and there may be added ions such as a $Cl^-$, $Ca^{2+}$ or $Mg^{2+}$ in the form of NaCl, $MgCl_2$, $MgSO_4$, $CaCl_2$ or $CaCl_2 \cdot H_2O$ as a human α-amylase activating agent. These additives may be added alone or in combination of the two or more. These components may be added at an appropriate step during the preparation of the system.

When a maltooligosaccharide represented by the general formula (II) wherein R represents a hydrogen atom or a moiety of a monosaccharide is employed as substrate, the quantitative determination of glucose, maltose or the other monosaccharides formed by an enzymatic reaction with the spectroscopic method can be done by adding enzymes generally used in the measurement system involved in the oxidation-reduction reaction of NAD(P)→NAD(P)H or NAD(P)H→NAD(P) such as glucose-6-phosphate dehydrogenase (e.g. the one derived from Leuconostoc mesenteroides), maltose phosphorylase (e.g. the one derived from Lactobacillus brevis), hexokinase (e.g. the one derived from yeast), β-phosphomutase (e.g. the one derived from rabbit muscle), sorbitol dehydrogenase (e.g. derived from sheep liver), NAD(P) [or NAD(P)H] and ATP.

It is more preferable that the maltooligosaccharide of the formula (II) wherein R is an aromatic chromogenic group is employed as substrate, because the use of said enzymes is not necessary and the absorbance method may be applied.

DESCRIPTION OF THE PREFERRED EMBODIMENTS

The process of the present invention is now explained with reference to preferred embodiments.

First of all, the reaction rate constants ($k_p$, $k_s$) are determined by using a maltooligosaccharide derivative represented by the present formula (II) as a substrate and P-type and S-type α-amylase preparations having a known activity according to the conventional method.

Also, P-type and S-type α-amylase preparations having a known activity are used, $6^3$-deoxymaltotriose represented by the formula (I) is added in various concentrations to the same substrate to determine the concentration at which the difference of the inhibition constants between the inhibitors to the above-described P-type and S-type α-amylases maximizes, and the inhibition constants (a, b) to P-type and S-type α-amylases in the concentration are obtained by the usual method.

Next, the differential determination method includes the two channel method (twice measuring method) and the double kinetic method (single measuring method, simultaneous two item analysis), and the former method is now explained.

To a sample having α-amylase activity are added, if necessary, α-glucosidase and/or glucoamylase as a coupled enzyme, in an amount of 5–1,000 units/ml, preferably 10–500 units/mi. If the substrate contains β-anomer, further β-glucosidase in an amount of 0.5–30 units/ml, preferably 1–15 units/ml is added therein. At the same time or then, 0.1–10 mM, preferably 0.3–5 mM of the substrate is added together with a buffer, and the mixture was reacted under a condition at a temperature of 25°–45° C., preferably 35°–40° C., and at a pH value of 4–10, preferably 6.5–7.5 for at least 1 minute, preferably 2–10 minutes. The variation of absorbance (T) of the aromatic chromogenic compound thus obtained is directly or after the adjustment of pH measured continuously or intermittently at an appropriate wavelength.

Also, the variable absorbances (W) are measured in the same manner as above except that the inhibitor is added to the same substrate as above in a concentration at which the difference of the inhibition constants of P-type and S-type amylases in the measurement system maximalizes.

Next, referring to the latter method, the variable absorbances (T') are measured in the same manner as above, and said inhibitor is added to the measurement system in a concentration at which the difference of the inhibiting constants maximalizes to measure the variable absorbances (W).

In this case, T is represented by the following equation:

$$T=T' \times (T' \text{ total liquid amount at the measurement}/W \text{ total liquid amount at the measurement})$$

In this connection, the inhibitor may be added directly to the substrate solution or the measurement system or may also be used by adding it to a coupled enzyme used.

In the case of the compound represented by the general formula (II) wherein R represents a hydrogen atom or a moiety of an monosaccharide, procedures can be followed in the same manner as in the case wherein R is an aromatic chromogenic group after the enzyme relating to the absorbance system and the other necessary components have been added.

The values thus obtained can be substituted for $k_p$, $k_s$, a, b, T and W in the equations (3) and (4), and thus the P-type α-amylase activity (P) and the S-type α-amylase activity (S) in a sample can be obtained.

$6^3$-deoxymaltotriose represented by the formula (I) which is used as an inhibitor in the present invention exhibits an extremely large difference between the inhibition constants to the two α-amylase isoenzymes and thus has an advantage that differential determination of isoenzyme activities in human α-amylase can be carried out efficiently, in an simple operation with an improved precision as compared with the conventional methods. Thus, the process of the present invention is suitable to the determination method for the diagnosis of diseases in which P-type α-amylase and S-type α-amylase must be quantitatively determined separately.

Also, the double kinetic method (single measuring method, simultaneous two item analysis) may be applied as the differential determination method of the present invention. This method is preferred in that measurement can be carried out as described in Examples below with a sample, substrate and a coupled enzyme in a half amount in a short time as compared with the two channel method (double measuring method).

The present invention is now explained in more detail with reference to Examples.

In the Examples, N3G5-CNP means 2-chloro-4-nitrophenyl $6^5$-azido-$6^5$-deoxy-β-D-maltopentaoside, DOG3 means $6^3$-deoxymaltotriose, and G5-CNP means 2-chloro-4-nitrophenyl β-D-maltopentaoside.

Also, the wavelength of a maximum absorbance was measured in methanol and specific rotation was measured with D-ray at 25° C., unless otherwise specified.

Informative Example 1: Preparation of N3G5-CNP (1) Preparation of 6-O-tosyl-β-cyclodextrin A commercially available β-cyclodextrin (Wako Pure Chemical Industries, Ltd., 50.0 g, 44.1 mmol) was dissolved in 500 ml of pyridine, and 33.3 g (175 mmol) of tosyl chloride was added. The mixture was reacted with stirring at room temperature for 4 hours. To the reaction mixture were then added 250 ml of water and 1 liter of n-butanol. The mixture was concentrated to a volume of ½ under a reduced pressure and poured with stirring into 500 ml of acetone to precipitate a solid product, which was filtered with a glass filter and washed twice with 200 ml of acetone. The product separated by filtration was purified by ODS column chromatography, and the aimed fraction eluted with an ethanol-water mixture (volume ratio 1: 9) was concentrated and recrystallized from water to give 25.3 g of 6-O-tosyl-β-cyclodextrin (19.6 mmol, yield: 44.4%).

Melting point (°C.): 172.0–174.0 (dec.)

IR spectrum (cm$^{-1}$): 3400, 2930, 1642, 1632, 1600, 1424, 1360, 1300, 1178, 1156, 1078, 1028

NMR spectrum (200 MHz) ppm (DMSO-$d_6$): 2.44 (3H, s), 3.15–4.45 (m), 4.76 (2H, br.s), 4.85 (5H, br.s), 7.44 (1H, d, J=8.8 Hz), 7.75 (1H, d, J=8.8 Hz)

(2) Preparation of 6-azido-6-deoxy-β-cyclodextrin

6-O-tosyl-β-cyclodextrin (16.9 g, 13.1 mmol) obtained in the above section (1) was dissolved in a mixture of 500 ml of water and 250 ml of 1,4-dioxane, 34.1 g (525 mmol) of sodium azide was added, and the mixture was reacted at 85° C. for 4 hours. The reaction mixture was then concentrated under reduced pressure into a volume of ½, and purified by ODS column chromatography. The aimed fraction eluted with a mixture of ethanol-water (volume ratio 1:9) was concentrated and recrystallized from water to give 14.3 g of 6-azido-6-deoxy-β-cyclodextrin (12.3 mmol, yield: 93.9%).
Melting point (°C.): 215.0–218.0 (dec.)
IR spectrum (cm$^{-1}$): 3390, 2920, 2120, 1642, 1414, 1370, 1340, 1304, 1156, 1080, 1030
High performance liquid chromatography [TSK gel Amide-80 column (4.6 mm ID×250 mm) manufactured by Tosoh Corporation, RI detector, eluent: acetonitrile/water=3:2 (v/v), flow rate: 1.0 ml/min.]: $t_R$=6.6 min.
Specific rotation [α]: (c 0.510, 1,4-dioxane/H$_2$O=1:1 (v/v); +145°
Elementary analysis: for C$_{42}$H$_{69}$N$_3$O$_{34}$

|  | C | H | N |
|---|---|---|---|
| Theoretical (%) | 43.49 | 6.00 | 3.62 |
| Calculated (%) | 43.28 | 6.11 | 3.53 |

(3) Preparation of 6$^5$-azido-6$^5$-deoxy-D-maltopentaose 6-azido-6-deoxy-β-cyclodextrin (25 g, 21.6 mmol) obtained in the same procedure as in (2) was poured with stirring into 1.0 liter of a 10 mM phosphate buffer (pH 7.8) which has been heated at 40° C. and dissolved completely. 490 units of cyclodextrinase obtained in the method described below was added, and the mixture was reacted with stirring at 40° C. for 2 hours. After the reaction had been completed, the reaction mixture was heated with stirring at 80° C. for 10 minutes. The reaction mixture was then cooled to room temperature, filtered with RADIOLITE (#100) and a membrane filter (0.45 μm), and then concentrated under reduced pressure to 115 ml. The concentrate thus obtained was purified by ODS column chromatography, eluted with a mixture of ethanol-water [0% (v/v)→35% (v/v) gradient] and concentrated to give 11.6 g of a 6$^m$-azidized maltoheptaose (m=an integer of 1–7) (9.86 mmol, yield: 45.6%).

The product was then dissolved into 250 ml of 20 mM acetate buffer (pH 4.5) with stirring, and 8 mg of glucoamylase [250 units, Seikagaku Corporation] was further added to the solution. The mixture was reacted with stirring at 40° C. for 4 hours. After the reaction was completed, the reaction mixture was heated with stirring at 90° C. for 20 minutes. It was then cooled down to room temperature, filtered through a membrane filter (0.45 μm) and concentrated under reduced pressure to a volume of 55 ml. The concentrate thus obtained was purified by activated charcoal column chromatography, eluted with a mixture of ethanol-water (5%→45% gradient), and the fraction eluted with ca. 30% ethanol was lyophilized to give 1.79 g of 6$^5$-azido-6$^5$-deoxy-D-maltopentaose (2.10 mmol, yield: 21.3%).
Melting point (°C.): 176.0–179.0
IR spectrum (cm$^{-1}$): 3400, 2920, 2110, 1628, 1406, 1360, 1278, 1240, 1144, 1076, 1022
NMR spectrum (200 MHz) ppm (D$_2$O): 2.80–4.00 (m), 4.64 (0.5H, d, J=8.0 Hz), 5.23 (0.5H, d, J=3.5 Hz), 5.35 (4H, d, J=3.5 Hz)
High performance liquid chromatography [TSK gel Amide-80 column (4.6 mm ID×250 mm) manufactured by Tosoh Corporation, RI detector, eluent: acetonitrile/water=3:2 (v/v), flow rate: 1.0 ml/min.]: $t_R$=6.9 min.

Specific rotation [α]: (c 0.544, H$_2$O); +169°
Elementary analysis: for C$_{30}$H$_{51}$N$_3$O$_{25}$

|  | C | H | N |
|---|---|---|---|
| Theoretical (%) | 42.21 | 6.02 | 4.92 |
| Calculated (%) | 42.03 | 6.13 | 4.69 |

(4) Preparation of N3G5-CNP

6$^5$-azido-6$^5$-deoxymaltopentaose (5.0 g, 5.86 mmol) obtained in the same manner as in (3) above was dissolved in 100 ml of pyridine, 50 ml (529 mmol) of acetic anhydride was added, and the mixture was reacted at room temperature for 2 days. After pyridine, acetic anhydride and acetic acid in the reaction mixture were evaporated, the residue without purification was dissolved in 30 ml of dichloromethane, 556 μl (5.86 mmol) of phosphorus tribromide and 211 μl (11.7 mmol) of water were added to the solution, and the mixture was reacted with stirring at room temperature for 20 hours. To the reaction mixture was added 18.6 g (135 mmol) of anhydrous potassium carbonate, and the mixture was reacted with stirring at room temperature for 15 minutes. Insolubles were separated with a glass filter and washed thrice with 200 ml of dichloromethane. The filtrate and the washes were combined, and dichloromethane was removed by evaporation. The residue without purification was dissolved in 100 ml of acetonitrile, 5.09 g (29.3 mmol) of 2-chloro-4-nitrophenol followed by 6.80 g (29.3 mmol) of silver oxide (Ag$_2$O) was added to the solution, and the mixture was reacted with stirring at 35° C. for 17 hours. The reaction mixture was passed through a glass filter, and the solid was washed thrice with 50 ml of dichloromethane. The filtrate and the washes were combined and concentrated under reduced pressure to remove acetonitrile and dichloromethane contained in the filtrate. After 300 ml of dichloromethane was added to the residue and the mixture was filtered through a cotton plug, insolubles were washed once with 200 ml of a 0.5N aqueous sodium hydroxide solution and thrice with 200 ml of saturated saline. The filtrate and washes were combined and dried over 10 g of anhydrous sodium sulfate, filtered through a cotton plug, concentrated under reduced pressure to remove the dichloromethane. The residue were directly suspended in a mixture of 60 ml of methanol, 30 ml of a 28 wt % aqueous ammonia and 15 ml of water, and the suspension was reacted with stirring at 35° C. for 20 hours. The reaction mixture was then concentrated under reduced pressure to remove water and methanol contained in the reaction mixture. The residue thus obtained was purified by ODS gel column chromatography, and the aimed fraction eluted with a mixture of ethanol-water (volume ratio 1:4) was concentrated and recrylstallized from water to give 2.47 g of the aimed N3G5-CNP (2.45 mmol, yield: 41.8%).
Melting point (°C.): 130.0–135.0 (dec.)
UV-visible spectrum: maximum absorption wavelength [λmax] (nm)=290 (log ϵ=3.98), 227 (log ϵ=3.99), 209 (log ϵ=4.20)
IR spectrum (cm$^-$): 3410, 2930, 2110, 1584, 1520, 1484, 1274, 1150, 1078, 1024
NMR spectrum (200 MHz) ppm (DMSO-d$_6$): 3.05–3.90 (m), 4.20–4.55 (m), 4.74 (1H, br d, J=4.8 Hz), 4.96 (1H, br d, J=5.4 Hz), 5.05 (2H, d, J= 3.7 Hz), 5.10 (2H, d, J=3.7 Hz), 5.25 (1H, d, J=7.6 Hz), 5.25–5.60 (m), 7.47 (1H, d, J=9.3 Hz), 8.19 (1H, dd, J=9.3 Hz, 2.7 Hz), 8.29 (1H, d, J=2.7 Hz)

High performance liquid chromatography [TSK gel Amide-80 column (4.6 mm ID×250 mm) manufactured by Tosoh corporation, RI detector, eluent: acetonitrile/water=3:1 (v/v), flow rate: 1.0 ml/min.]: $t_R$=6.7 min.

Specific rotation: (c 0.516, $H_2O$); +92.4°

Elementary analysis: for $C_{36}H_{53}ClN_4O_{27}$

|  | C | H | N |
| --- | --- | --- | --- |
| Theoretical (%) | 42.84 | 5.29 | 5.55 |
| Calculated (%) | 42.88 | 5.31 | 5.59 |

Informative Example 2: Preparation of DOG3

(1) Preparation of 6-deoxy-β-cyclodextrin

After 1.27 g (0.985 mmol) of 6-O-tosyl-β-cyclodextrin obtained in the paragraph (1) in Informative Example 1 was dissolved in 20 ml of dimethylsulfoxide (DMSO), 384 mg (10.2 mmol) of sodium borohydride ($NaBH_4$) was added, and the mixture was reacted at 50° C. for 12 hours. Next, 1,000 ml of water was added to the reaction mixture, and the mixture was subjected to ODS column chromatography to remove the DMSO. The aimed fraction eluted with a mixture of ethanol-water (volume ratio 1:9) was concentrated and recrystallized from methanol to give 839.6 mg of 6-deoxy-β-cyclodextrin (0.750 mmol, yield: 76.1%).

Melting point (°C.): 280.0–281.0 (dec.)

IR spectrum ($cm^{-1}$): 3370, 2920, 1152, 1080, 1020

NMR spectrum (200 MHz) ppm (DMSO-$d_6$): 1.20 (3H, d, J=6.1 Hz), 2.80–4.05 (m), 4.84 (7H, br s)

Elementary analysis: for $C_{42}H_{70}O_{34}$

|  | C | H |
| --- | --- | --- |
| Theoretical (%) | 45.08 | 6.31 |
| Calculated (%) | 44.99 | 6.45 |

(2) Preparation of DOG3

Fifteen grams of 6-deoxy-β-cyclodextrin obtained in the same manner as described in (1) was added with stirring to 1.0 liter of a 100 mM phosphate buffer (pH 7.0) and dissolved completely. To this solution was added 24 units of cyclodextrinase obtained by the method described below, and the mixture was reacted with stirring at 40° C. for 48 hours. After the reaction was completed, hydrochloric acid was added to the reaction mixture to adjust pH to about 2.0 and to stop the reaction. The mixture was neutralized by the addition of a sodium hydroxide solution and passed through an ODS column to adsorb the unreacted 6-deoxy-β-cyclodextrin thereon and to give an eluted fraction. This procedure was conducted repeatedly to treat 63 g in total of 6-deoxy-β-cyclodextrin. After the eluted fraction was mixed with a 1/10 volume of a 100 mM acetate buffer (pH 4.5), it was further adjusted with 100 mM acetic acid to adjust pH to 4.5. Subsequently, 2,500 units of glucoamylase was added to conduct enzyme reaction at 40° C. for 8 hours, hydrochloric acid was added to the mixture to adjust pH to about 2.0 and to stop the reaction, and a sodium hydroxide solution was added to neutralize the reaction mixture. The reaction mixture was then passed through an activated charcoal column, 6-deoxymaltooligosaccharide was eluted with ethanol gradients of 0–35% of which an ethanol elution fraction with ca. 21% ethanol was lyophilized to give about 1.1 g of $6^3$-deoxy-D-maltotriose having a purity of about 98%.

IR spectrum ($cm^{-1}$): 3400, 2950, 1690, 1146, 1042

NMR spectrum (200 MHz) ppm ($D_2O$): 1.28 (3H, d, J=6.1 Hz), 3.17 (1H, t, J=8.9 Hz), 3.29 (1H, t, J=8.9 Hz), 3.50–4.05 (m), 4.65 (ca. 0.5H, d, J=7.8 Hz), 5.25 (ca. 0.5H, d, J=3.7 Hz), 5.27 (1H, d, J=3.0 Hz), 5.36 (1H, d, J=3.9 Hz)

High performance liquid chromatography [TSK gel Amide-80 column (4.6 mm ID×250 mm) manufactured by Tosoh corporation, RI detector, eluent: acetonitrile/water=3:2 (v/v), flow rate: 1.0 ml/min.]: $t_R$ =5.9 min.

Elementary analysis: for $C_{18}H_{32}O_{15}$

|  | C | H |
| --- | --- | --- |
| Theoretical (%) | 44.26 | 6.60 |
| Calculated (%) | 44.28 | 6.58 |

Informative Example 3: Preparation of cyclodextrinase

A 100 ml portion of a liquid culture medium (tap water being used as water, pH 7.0) comprising 1% (w/v) β-cyclodextrin, 1% (w/v) peptone, 0.5% (w/v) NaCl and 0.1% (w/v) yeast extract was placed in a 500 ml Sakaguchi flask and subjected to pasteurization at 120° C. for 20 minutes. A platinum loop amount of a stock slant of Bacillus sphaericus E-244 (FERM BP-2458) was inoculated in the medium and shake cultured at 30° C. for 1 day. 50 ml portion of the culture medium was inoculated in a 3,000 ml container containing 2,000 ml of a culture medium having the same composition and prepared by the same pasteurization as described above and subjected to aeration- agitation fermentation under a condition of 30° C., 1 vvm and 350 rpm for 2 days. After the fermentation was completed, the bacterial cell was separated from the culture by centrifugation at 8,000 rpm for 20 minutes, suspended into 500 ml of a 10 mM phosphate buffer (pH 7.0) containing 2% (w/v) Triton X-100, and the suspension was stirred at 25° C. for one day. After the residual bacterial cells were removed from the suspension by centrifugation at 12,000 rpm for 20 minutes, the supernatant was dialyzed against a 10 mM phosphate buffer (pH 7.0), and the dialyzed product was centrifuged at 12,000 rpm for 20 minutes to remove the insolubles. The supernatant was used as a crude enzyme solution (1).

After about 500 ml of the crude enzyme solution (1) (total activity, 200 units; amount of protein, 2083 mg; specific activity, 0.1; pH 7.0) was next placed on a DEAE Sepharose charged column equilibrated with a 10 mM phosphate buffer (pH 7.0) (diameter of 34×170 mm) and the enzyme was adsorbed on it, eluation was carried out with a gradient of 0–0.5 M NaCl. The active fractions thus obtained were combined to give 105 ml of a crude enzyme solution (2) (total activity, 145 units; specific activity, 0.58, yield, 72.5%).

Then, a 20 ml portion of the crude enzyme solution (2) (total activity, 31 units; amount of protein, 29 mg) was placed on an Ether 5PW charged column equilibrated with a 100 mM phosphate buffer (pH 7.0) containing 1M sodium sulfate (diameter of 21.5×150 mm) and the enzyme was adsorbed, eluation was carried out with a gradient of 1M–0M sodium sulfate. The active fractions thus obtained were combined to give 50 ml of a crude enzyme solution (3) (total activity, 72 units; specific activity, 2.93; yield, 36%) (see Japanese Patent Kokai No. 3-15384).

EXAMPLE 1

(1) Measurement of the Km value of a substrate N3G5-CNP for measuring α-amylase activity (a) Preparation of N3G5-CNP solution In a 50 mM phosphate buffer (pH 7.0) containing 40 mM NaCl and 2 mM $MgCl_2$ was dissolved N3G5-CNP obtained in Informative Example 1 to prepare substrate solutions for measuring α-amylase activity in a concentration of 0.16, 0.32, 0.48, 0.64, 0.80 and 0.96 mM.

(b) Preparation of coupled enzyme solution

A commercially available glucoamylase derived from Rhizopus sp. and β-glucosidase derived from almond were mixed and dissolved in a 50 mM phosphate buffer (pH 7.0) containing 40 mM NaCl and 2 mM $MgCl_2$ to the concentration of the glucoamylase and β-glucosidase being 163 units/ml and 16.3 units/ml, respectively. In this connection, these commercially available glucoamylase and β-glucosidase used were manufactured by Toyobo Co., Ltd.

(c) Preparation of α-amylase solution

Each of commercially available human P-type α-amylase and human S-type α-amylase was dissolved in distilled water to ensure that the concentration of each amylase was about 150 IU/liter.

The commercially available human α-amylases used were CARIBZYME AMY manufactured by International Reagents Corp., Japan.

The molecular extinction coefficient (ε) of 2-chloro-4-nitrophenol is defined 16,100 and for α-amylase activity the amount of enzyme which decomposes 1 μmol of G5-CNP at 37° C. for a minute is defined as 1 International Unit (IU) (and so forth).

(d) Measurement of Km

As for the human P-type α-amylase solution and human S-type α-amylase solution, 1.0 ml of a coupled enzyme solution was added to and stirred with 250 μl of the α-amylase solution, warmed to 37° C. for 1 minute, and 2.0 ml of each concentration of the N3G5-CNP solution was added and stirred, warmed to 37° C. for 2.5 minutes to measure the variable absorbances at 400 nm for 2 minutes. At the same time, a blank test was carried out with 250 μl of distilled water instead of the α-amylase solution. The measurements thus obtained were plotted by the Lineweaver-Burk method to calculate the Km value by the method of least squares. As a result, the Km values of N3G5-CNP to the human P-type and S-type α-amylases were 0.17 mM and 0.27 mM, respectively.

(2) Measurement of the reaction rate constants $k_p$ and $k_s$ of the substrate N3G5-CNP for measuring α-amylase activity, and a test for confirmation of linearity.

(a) Preparation of α-amylase solution

The commercially available human P-type and S-type α-amylases described above were dissolved in distilled water to prepare α-amylase solutions having a concentration of 541 IU/liter and 510 IU/liter, respectively. These solutions were used as stock solutions and diluted with distilled water to prepare six α-amylase solutions having a concentration of 100%, 80%, 50%, 30%, 20% and 10% (v/v).

(b) Preparation of the coupled enzyme solution

It was prepared in the same manner as in (b) of (1) described above.

(c) Preparation of the N3G5-CNP solution

The N3G5-CNP described above was dissolved in a 50 mM phosphate buffer (pH 7.0) containing 40 mM NaCl and 2 mM $MgCl_2$ so that the buffer has a concentration of the N3G5-CNP of 3.25 mM [final concentration (concentration in a measurement system, and the forth) 2.0 mM]. The concentration corresponds to 11.8 and 7.4 times of the Km value to the human P-type and S-type α-amylases and thus is a concentration which is sufficient for obtaining the maximum reaction rate.

(d) Confirmation of linearity and measurement of the $k_p$ and $k_s$ values

For six solutions of each of the human P-type α-amylase and the human S-type α-amylase, 1.0 ml of the coupled enzyme solution was added to and stirred with 250 μl of the α-amylase solution and warmed to 37° C. for 1 minute, respectively. 2.0 ml of N3G5-CNP solution was added and stirred, and the mixture was warmed to 37° C. for 2.5 minutes to measure the variable absorbances at 400 nm for 2 minutes. A blank test was carried out with 250 μl of distilled water instead of the α-amylase solution. As a result, linearity was confirmed up to the concentration of 541 IU/liter for the human P-type α-amylase (r=0.999) and the concentration of 510 IU/liter for the human S-type α-amylase (r=0.998).

The following equations were also derived from the inclination of the line obtained by the method of least squares:

$$k_p = 1.1 \times 10^{-3}$$

$$k_s = 1.1 \times 10^{-3}$$

(3) Test of measuring the inhibiting constant to the human P-type α-amylase and the human S-type α-amylase of DOG3

(a) Preparation of a mixed solution of the substrate (N3G5-CNP) and the inhibitor DOG3

N3G5-CNP and DOG3 obtained in Informative Example 2 were dissolved in a 50 mM phosphate buffer (pH 7.0) containing 40 mM NaCl and 2 mM $MgCl_2$ so that the N3G5-CNP has a concentration of 3.25 mM (final concentration of 2.0 mM) and DOG3 has seven concentrations of 0.05, 0.11, 0.54, 1.09, 2.16, 3.25, 5.41 mM (final concentrations of 0.03, 0.07, 0.33, 0.67, 1.33, 2.00 and 3.33 mM, respectively).

(b) Preparation of α-amylase solution

The commercially available human P-type α-amylase and human S-type α-amylase were dissolved in distilled water so that they have a concentration of about 150 IU/liter.

(c) Preparation of coupled enzyme solution

It was prepared in the same manner as described in (b) in the section (1).

(d) Measurement of inhibition constant

After 250 μl of the α-amylase solution was admixed with 1.0 ml of the coupled enzyme solution and warmed to 37° C. for 1 minute, 2.0 ml of each of the mixtures (having 7 concentration) of the substrate (N3G5-CNP) and the inhibitor DOG3 was added, stirred and warmed to 37° C. for 2.5 minutes, and the variable absorbance in each sample at 400 nm was measured for 2 minutes.

Figure 1:
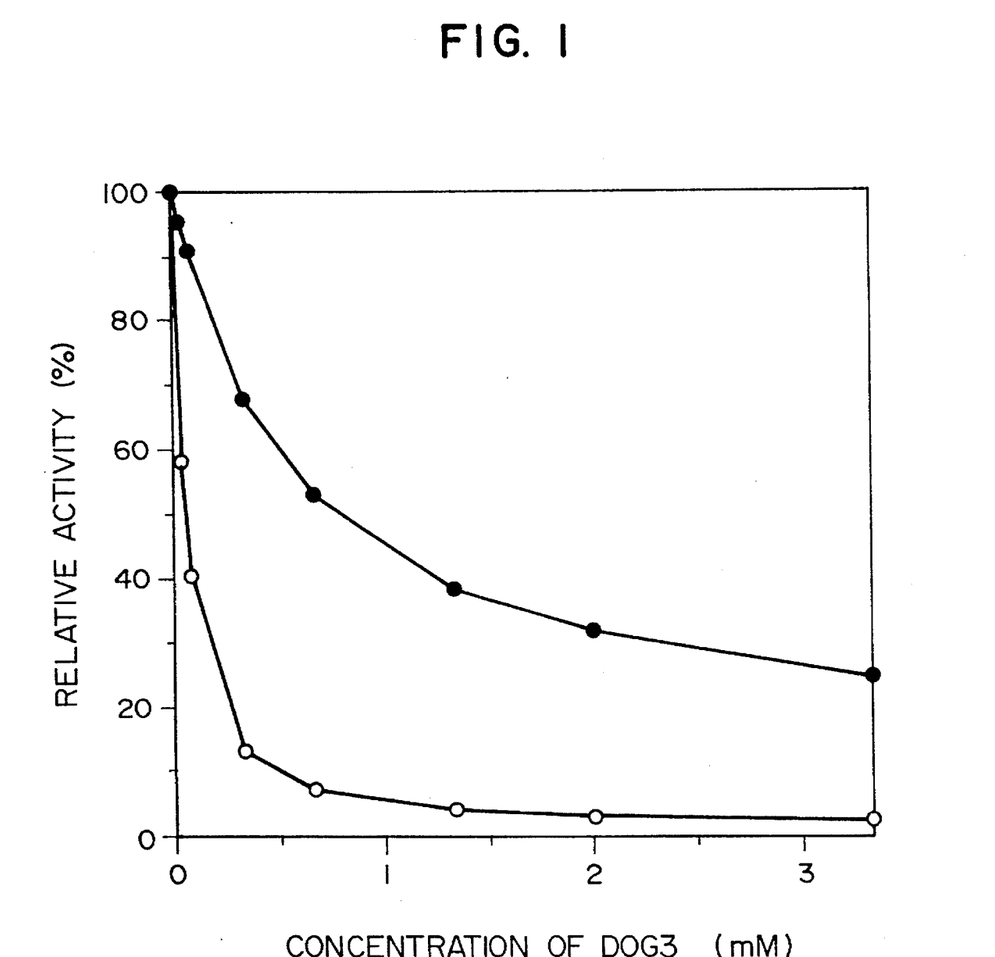
FIG. 1 is a graph which illustrates the relationship between the various concentrations of 6³-deoxymaltotriose (DOG3) as inhibitor and the relative activities of P-type and S-type α-amylases, in Examples of the process according to the present invention.

The activities of human P-type α-amylase and human S-type α-amylase containing 0 mM of DOG3 (without DOG3) were regarded as 100% and the relative activities of human P-type α-amylase and human S-type α-amylase in different concentrations of DOG3 were obtained from each determined value as mentioned above. The results are shown in FIG. 1. In this connection, a open circle means P-type α-amylase and a closed circle means S-type α-amylase.

Next, relative activities of the human P-type and S-type α-amylases (13.1%, 67.9%, respectively) to a concentration of DOG3 (0.33 mM) at which the difference of the relative activities maximalizes (0.548), and the inhibition constants (a, b) were obtained from these values.

$$a = 1 - 0.131 = 0.869$$

b=1−0.679=0.321

The values of $k_p$, $k_s$, a and b are thus obtained, and the activities of the human P-type and S-type α-amylases (P, S) are obtained by substituting the variable absorbances measured for T and W in the equations (3) and (4).

(4) Differential determination test

Human P-type and S-type α-amylases having a known activity were mixed in various ratios, and the compatibility of the theoretical value obtained on the basis of the mixing ratio and the calculated value obtained from the equations (3) and (4) was observed about the use of the N3G5-CNP as substrate and the DOG3 as inhibitor.

(a) Preparation of the substrate (N3G5-CNP) solution

The substrate (N3G5-CNP) was dissolved in a 50 mM phosphate buffer (pH 7.0) containing 40 mM NaCl and 2 mM $MgCl_2$ so that the substrate has a concentration of 3.25 mM (final concentration 2.0 mM).

(b) Preparation of the mixture solution of the substrate (N3G5-CNP) and the inhibitor (DOG3)

The N3G5-CNP and DOG3 were dissolved in a 50 mM phosphate buffer (pH 7.0) containing 40 mM NaCl and 2 mM $MgCl_2$ so that the substrate and the inhibitor has a concentration of 3.25 mM (final concentration 2.0 mM) and 0.54 mM (final concentration 0.33 mM), respectively.

(c) Preparation of the coupled enzyme solution

It was prepared in the similar manner as described in (b) in section (1).

(d) Preparation of α-amylase isoenzyme test solution

The commercially available human P-type and S-type α-amylases were dissolved in distilled water to prepare an α-amylase solutions having a theoretical value which corresponds to (P:S)=(10:0) and (0:10). The activities are within the range wherein the linearity tested in the aforementioned section (2) is maintained.

These solutions were employed as the stock solutions, and the mixed solutions of the P-type and S-type α-amylases were mixed in the following mixture ratio by volume to prepare eleven α-amylase isoenzyme test solutions: (P:S)= (10:0), (P:S)=(9:1), (P:S)=(8:2), (P:S)=(7:3), (P:S)=(6:4), (P:S)=(5:5), (P:S)=(4:6), (P:S)=(3:7), (P:S)=(2:8), (P:S)= (1:9) and (P:S)=(0:10)

(e) Differential determination test

After 1.0 ml of the coupled enzyme solution was mixed with 250 µl of each of α-amylase isoenzyme test solutions and the mixture was warmed to 37° C. for 1 minute, 2.0 ml of the N3G5-CNP solution or a mixture solution of N3G5-CNP and DOG3 was added and warmed to 37° C. for 2.5 minutes to measure the variable absorbances (ΔOD) at 400 nm. The blank test was conducted with use of 250 µl of distilled water instead of the α-amylase isoenzyme test solutions to obtain the values of T and W. The activity value obtained from the activity prior to mixing and the mixing ratio is used as the theoretical activity, and the values obtained from calculation by substituting the values of $k_p$, $k_s$, a, b, T and W for the equations (3) and (4) are used as the calculated activities (found values). The test results are shown in Table 1. The unit of activity is IU/liter.

TABLE 1

| | P-type α-amylase | | S-type α-amylase | |
|---|---|---|---|---|
| | Theoretical | Calculated | Theoretical | Calculated |
| 10:0 | 183 | 183 | 0 | 0 |
| 9:1 | 165 | 168 | 16 | 14 |
| 8:2 | 147 | 151 | 32 | 33 |

TABLE 1-continued

| | P-type α-amylase | | S-type α-amylase | |
|---|---|---|---|---|
| | Theoretical | Calculated | Theoretical | Calculated |
| 7:3 | 128 | 133 | 47 | 47 |
| 6:4 | 110 | 106 | 63 | 66 |
| 5:5 | 92 | 90 | 79 | 79 |
| 4:6 | 73 | 70 | 95 | 93 |
| 3:7 | 55 | 55 | 111 | 106 |
| 2:8 | 37 | 32 | 126 | 127 |
| 1:9 | 18 | 18 | 142 | 141 |
| 0:10 | 0 | 0 | 158 | 158 |

It is found from Table 1 that calculated (found) values and the theoretical values have a high correlation.

EXAMPLE 2

Differential quantitative determination of α-amylase activity was carried out on human serum having α-amylase activities.

l (1) The differential determination according to the present process (2-channel method)

(a) Preparation of the substrate (N3G5-CNP), (b) preparation of the mixture of the substrate (N3G5-CNP) and the inhibitor (DOG3), and (c) preparation of a coupled enzyme solution were carried out in the same manner as in (a)–(c) of (4) in Example 1.

(d) α-amylase test solution

Human sera (50 samples) having α-amylase activities.

(e) Differential quantitative determination

Procedures were carried out in the same manner as in (e) of (4) in Example 1 except that 250 µl of human serum was used instead of the α-amylase isoenzyme test solution. The values of $k_p$, $k_s$, a and b as well as T and W obtained herein were substituted for the equations (3) and (4) to obtain the values of P and S (IU/liter).

(2) Method using the wheat-germ inhibitor (a) Preparation of the substrate (N3G5-CNP) solution and (b) α-amylase test solution are the same as (a) and (d) in the above-mentioned (1).

(c) Preparation of the mixture of a coupled enzyme and a wheat-germ inhibitor

One vial of a wheat-germ inhibitor [manufactured by Seikagaku Corporation, 8 AIU (1 AIU means the amount sufficient for inhibiting 50% of a human S-type amylase (2 units/liter)) (the blue starch method)] was dissolved in 50 ml of a coupled enzyme solution prepared in the same manner as in (b) of (1) in Example 1.

(d) Differential quantitative determination

A 1.0 ml portion of the mixed solution prepared in (c) was admixed with 250 µl of human serum, and warmed to 37° C. for 1 minute. The N3G5-CNP solution (2.0 ml) was admixed in said mixture and warmed to 37° C. for 2.5 minutes, and thereafter the variable absorbances (ΔOD) at 400 nm were measured for 2 minutes. A blank test was carried out with 250 µl of distilled water in place of the α-amylase test solution to obtain the value of W with this method.

On the other hand, procedures were carried out in the same manner as described above except that 1.0 ml of the coupled enzyme solution alone was used on behalf of the mixed solution in (c) to obtain the value of T with this method.

The values of $k_p$, $k_s$, a and b in the wheat-germ inhibitor method were $1.1 \times 10^{-3}$, $1.1 \times 10^{-3}$, 0,262 and 0.726 as a result of the measurement. These values as well as those of T and W obtained in this method were substituted for the equations (3) and (4) to obtain the values of P and S (IU/liter).

Figure 2:
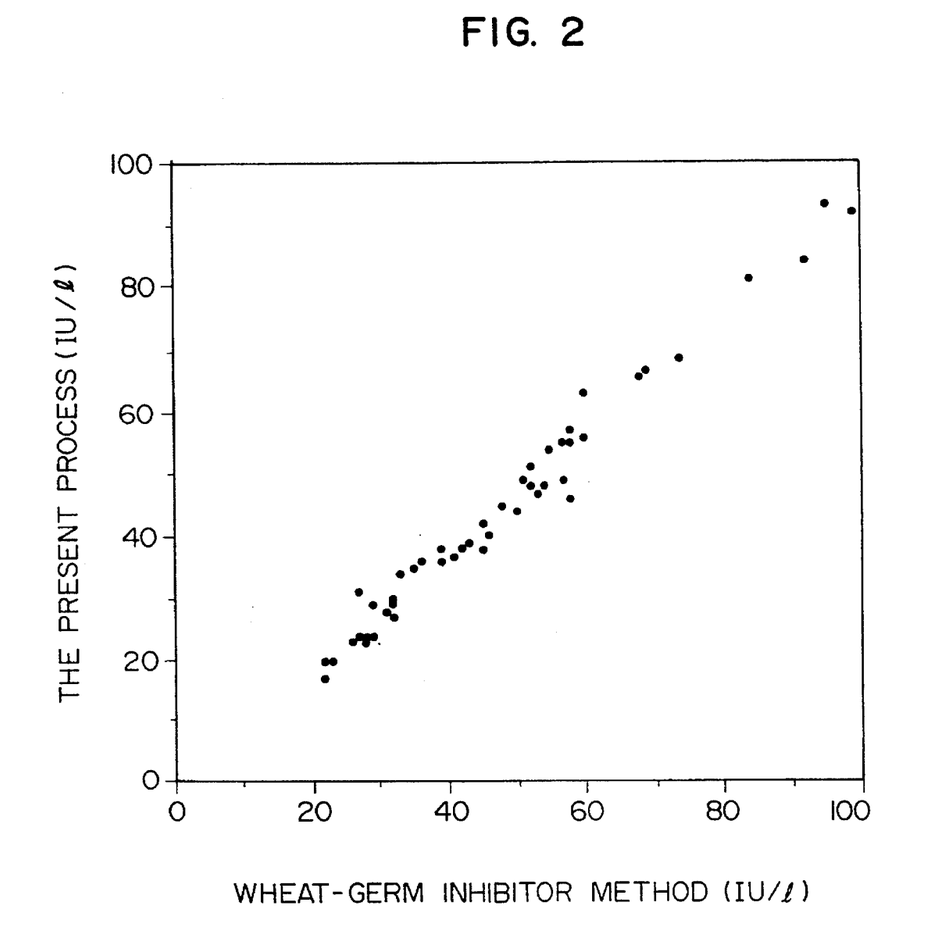
FIG. 2 is a graph which illustrates the correlation between the measurements of the P-type α-amylase activities according to the present process and those according to the wheat-germ inhibitor method.

(3) The graph in which the values of P obtained by the present differential determination process and the values of P obtained by the wheat-germ inhibitor method is illustrated in FIG. 2. As a result, it is found that the both P values have a correlation of r=0.989, Y=0.962 X−1.469 and these two methods are well consistent with each other.

(4) Comparison of the measurement errors in the present differential determination process with use of the other α-amylase test solution and in the wheat-germ inhibitor method.

P-type α-amylase activity was measured in the same manner as the differential determination method in (1) and (2) described above except that an Enzyme Reference [trade name of human α-amylase (P-type α-amylase: S-type α-amylase=1:1), manufactured by Wako Pure Industries, Ltd.] was used on behalf of human serum to compare the measurement errors in these methods. The results are shown in Table 2.

TABLE 2

|  | Present Process | Wheat-germ inhibitor method |
| --- | --- | --- |
| Number of Measurements | 30 | 30 |
| Average (IU/liter) | 141.2 | 143.9 |
| Standard deviation | 2.0 | 3.0 |
| Coefficient of variation (%) | 1.44 | 2.09 |

It can be seen from the coefficients of variation in Table 2 that α-amylase isoenzyme activities can be differentially determined with lesser measurement error and higher precision according to the present process as compared with the wheat-germ inhibitor method.

EXAMPLE 3

(1) Measurement of the Km value, reaction rate constants $k_p$ and $k_s$ of G5-CNP and the inhibition constants a and b of DOG3

The Km value and the reaction rate constants ($k_p$ and $k_s$) of G5-CNP and the inhibition constants a and b of DOG3 were measured in the same manner as in Example 1 except that a commercially available G5-CNP [manufactured by Daiichi Pure Chemicals Co., Ltd.] on behalf of N3G5-CNP as the substrate for measuring α-amylase was used and 406 units/liter of α-glucosidase [manufactured by Toyobo Co., Ltd.] was used on behalf of glucoamylase as a coupled enzyme.

As a result, the G5-CNP had the Km value, $k_p$ and $k_s$ of 0.45 mM, $1.2 \times 10^{-3}$ and $1.2 \times 10^{-3}$, respectively, and the DOG3 at the concentration of 0.50 mM had the a and b of 0.617 and 0.141, respectively.

(2) Differential quantitative determination (a) Preparation of the substrate G5-CNP solution It was prepared in the same manner as in (a) of (4) in Example 1 except that 3.25 mM of the aforementioned G5-CNP (final concentration 2.0 mM) was used on behalf of N3G5-CNP.

(b) Preparation of a mixed solution of the substrate (G5-CNP) and the inhibitor (DOG3)

It was prepared in the same manner as in (b) of (4) in Example 1 except that 3.25 mM (final concentration 2.0 mM) of the aforementioned G5-CNP was used on behalf of N3G5-CNP and the DOG3 was used in a concentration of 0.81 mM (final concentration 0.50 mM).

(c) Preparation of the coupled enzyme solution

It was prepared in the same manner as in (c) of (4) in Example 1 except that 406 units/ml of α-glucosidase [manufactured by Toyobo Co., Ltd.] instead of glucoamylase was used.

(d) α-amylase test solution

Human sera having α-amylase activities (50 samples)

(e) Differential quantitative determination test

Differential determination was carried out in the same manner as in (4) in Example 1 except that the solutions in (a)–(d) specified above on behalf of (a)–(d) of (4) in Example 1.

(3) Differential determination using N3G5-CNP as a substrate solution

Differential determination was carried out in the same manner as in (4) in Example 1 except that the α-amylase test solution in (d) specified above on behalf of the α-amylase isoenzyme test solution in (d) of (4) in Example 1.

Figure 3:
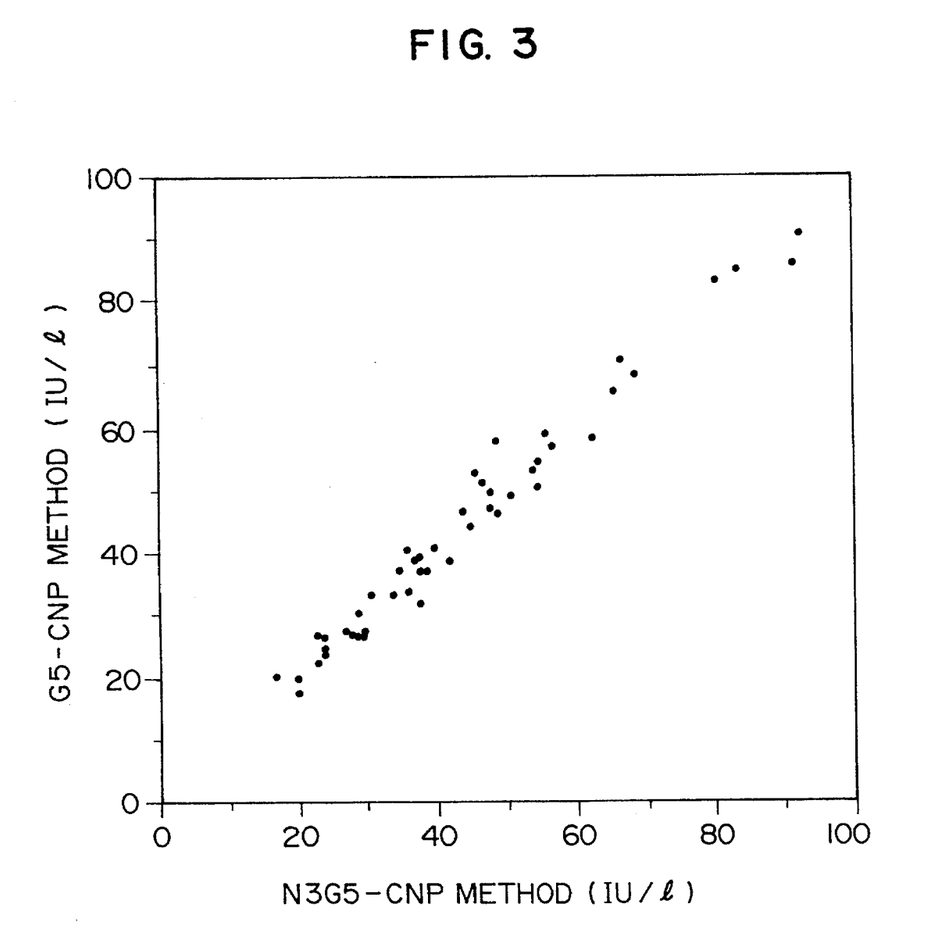
FIG. 3 is a graph which illustrates the correlation between the measurements of the P-type α-amylase activities according to the 2-chloro-4-nitrophenyl 6⁵-azido-6⁵-deoxy-β-D-maltopentaoside (N3G5-CNP) method in the present process and those according to the 2-chloro-4-nitrophenyl β-D-maltopentaoside (G5-CNP) method.

(4) A graph on which the P values obtained by the differential determination method in the aforementioned procedures (2) and (3) are plotted is illustrated in FIG. 3. As a result, it is found that the P values have a correlation of r=0.986, Y=0.974 X+1.155 and these two methods are well consistent with each other.

In addition, the G5-CNP method and the N3G5-CNP method in FIG. 3 mean the differential determination methods described in (2) and (3), respectively.

EXAMPLE 4

(1) Method for measuring T and W by the double kinetic method (single measuring method)

(a) α-amylase test solution

Human sera having α-amylase activities (70 samples)

(b) Preparation of the substrate (N3G5-CNP) solution

The N3G5-CNP was dissolved in a 50 mM phosphate buffer (pH 7.0) containing 40 mM NaCl and 2 mM $MgCl_2$ so as the concentration of the substrate to be 3.25 mM (final concentration 2.0 mM).

(c) Preparation of the coupled enzyme solution

It was prepared in the same manner as in the procedure (b) of (1) in Example 1 except that glucoamylase and β-glucosidase are used in a concentration of 181 units/ml and 18.1 units/ml, respectively.

(d) Preparation of the DOG3 solution

The DOG3 described above was dissolved in a 50 mM phosphate buffer (pH 7.0) containing 40 mM NaCl and 2 mM $MgCl_2$ so as the concentration to be 10.73 mM (final concentration 0.33 mM).

(e) Differential quantitative determination

The mixture of 0.9 ml of the coupled enzyme solution and 250 µl of each human serum was stirred and warmed at 37° C. for 1.0 minute, and 2.0 ml of the N3G5-CNP solution was then mixed. The resulting mixture was warmed at 37° C. for 1.0 minute, and the variable absorbances (AOD) at 400 nm were measured for 2 minutes. After 30 seconds, 0.10 ml of the DOG3 solution was further added to the measurement system solution. The resulting mixture was warmed at 37° C. for 1.5 minute, and the variable absorbances (ΔOD) at 400 nm were measured for 2 minutes. The blank test was carried out with 250 μl of distilled water on behalf of the α-amylase test solution to measure T' and W.

In this case, T=T'×3.15/3.25

Next, the values of P and S (IU/liter) were calculated by substituting the values of $k_p$, $k_s$, a and b obtained in Example 1 as well as the values of T and W obtained in this procedure for the aforementioned equations (3) and (4).

Figure 4:
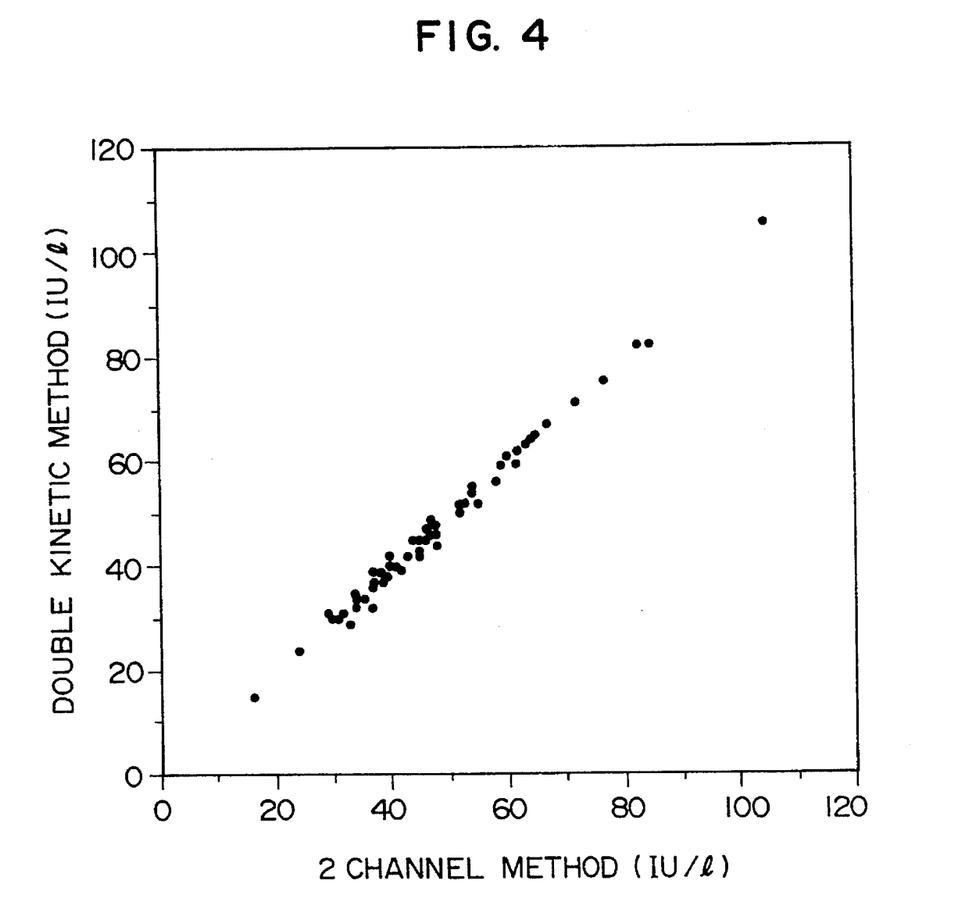
FIG. 4 is a graph which illustrates the correlation between the measurements of the P-type α-amylase activities according to the two channel method and those according to the double kinetic method in the present process.

(f) The graph in which the values of P thus obtained and those obtained in the same manner as in (1) in Example 2 (two channel method) are plotted is illustrated in FIG. 4. As a result, it is found that the P values have a correlation of r=0.9995, Y=0.994 X–0.415 and these two methods are well consistent with each other.

In other words, the present process is a process that the differential determination of α-amylase isoenzymes can be carried out with good precision in a single measurement, the substrate and the coupled enzyme can be measured with a half amount used in the two channel method, and thus it is also an excellent process economically.

What is claimed is:

1. In a process for differentially determining α-amylase isoenzyme activities, with use of a measured value of an α-amylase activity obtained by reacting a substrate for measuring the α-amylase activity with a sample and a measured value of an α-amylase activity obtained by reacting the same substrate and sample as above in the presence of an inhibitor which has different inhibiting constants against two kinds of α-amylase isoenzymes, the improvement which comprises using O-6-deoxy-α-D-glucopyranosyl-(1→4)-O-α-D-glucopyranosyl-(1→4)-D-glucose represented by the formula as an inhibitor.

2. A process according to claim 1, wherein said α-amylase is a human α-amylase, and the two α-amylase isoenzymes are an α-amylase derived from pancreatic juice and an α-amylase derived from salivary gland.

3. A process according to claim 2, wherein $6^3$-deoxymaltotriose represented by the formula (I) has a concentration from 0.01 to 10 mM in an α-amylase activity measuring system.

4. A process according to claim 1, wherein said process for differentially determining includes the double kinetic method or the two channel method.

5. A process according to claim 1, wherein said substrate for measuring α-amylase activity is a maltooligosaccharide derivative represented by the general formula wherein R represents a hydrogen atom, an aromatic chromogenic group or a saccharide group except glucose, $R^1$ and $R^2$, which may be the same or different, represent a halogen atom, a hydroxyl, an azido, an acyloxy, an alkyloxy, an aryloxy, an alkylsulfonyl, an arylsulfonyl, an alkylmercapto, an arylmercapto, an N-alkylcarbamoyloxy, an N-arylcarbamoyloxy, an alkyloxymethoxy or an aryloxymethoxy group, respectively, or $R^1$ and $R^2$ form together a substituted or unsubstituted methylenedioxy group, and n denotes an integer of 1–6.

6. A process according to claim 5, wherein said maltooligosaccharide derivative represented by the general formula (II) is maltopentaose, maltoheptaose, 2-chloro-4-nitrophenyl β-D-maltopentaoside, 2-chloro-4-nitrophenyl $4^5,6^5$-di-O-(N-ethyl)carbamoyl-β-D-maltopentaoside, 2-chloro-4-nitrophenyl $4^5,6^5$-di-O-methoxymethyl-β-D-maltopentaoside, 2-chloro-4-nitrophenyl $6^5$-azido-$6^5$-deoxy-β-D-maltopentaoside, 2-chloro-4-nitrophenyl $6^7$-chloro-$6^7$-deoxy-β-D-maltoheptaoside, 2-chloro-4-nitrophenyl α-D-maltotrioside, 4-nitrophenyl $6^5$-O-benzyl-α-D-maltopentaoside, 2-chloro-4-nitrophenyl $4^5,6^5$-O-benzylidene-β-D-maltopentaoside, phenolindo-3'-chlorophenyl $6^5$-O-toluenesulfonyl-β-D-maltopentaoside, $6^5$-chloro-$6^5$-deoxy-D-maltopentaose or 1-($4^6$-O-, $6^6$-O-dimethanesulfonyl-α-maltohexaosyl)-α -D-glucitol.

7. A process according to claim 6, wherein said maltooligosaccharide derivative represented by the general formula (II) is 2-chloro-4-nitrophenyl $6^5$-azido-$6^5$-deoxy-β-D-maltopentaoside or 2-chloro-4-nitrophenyl β-D-maltopentaoside.

8. A process according to claim 5, wherein said α-amylose activity is measured by the ratio of the reaction rate of α-amylase derived from human pancreatic juice to the reaction rate of α-amylase derived from human salivary gland to said substrate which is 0.6 or more.

* * * * *